United States Patent
Kárpáti et al.

(10) Patent No.: US 10,376,501 B2
(45) Date of Patent: *Aug. 13, 2019

(54) COMPLEXES OF LUMACAFTOR AND ITS SALTS AND DERIVATIVES, PROCESS FOR THE PREPARATION THEREOF AND PHARMACEUTICAL COMPOSITIONS CONTAINING THEM

(71) Applicant: Druggability Technologies IP Holdco Limited, Swatar (MT)

(72) Inventors: Richárd Balázs Kárpáti, Tatabánya (HU); Betti Szabóné Ordasi, Budapest (HU); Orsolya Basa-Dénes, Eger (HU); Erzsébet Réka Angi, Nagykovácsi (HU); Tamás Jordán, Öcsöd (HU); László Molnár, Biatorbágy (HU); Hristos Glavinas, Szeged (HU); Zsolt Ötvös, Csongrád (HU); Genovéva Filipcsei, Budapest (HU)

(73) Assignee: Druggability Technologies IP Holdco Limited, Msida (MT)

(*) Notice: Subject to any disclaimer, the term of this patent is extended or adjusted under 35 U.S.C. 154(b) by 0 days.

This patent is subject to a terminal disclaimer.

(21) Appl. No.: 15/496,246

(22) Filed: Apr. 25, 2017

(65) Prior Publication Data

US 2017/0326121 A1 Nov. 16, 2017

Related U.S. Application Data

(60) Provisional application No. 62/327,148, filed on Apr. 25, 2016.

(51) Int. Cl.

| *A01N 43/40* | (2006.01) |
|---|---|
| *A61K 31/443* | (2006.01) |
| *A61K 31/192* | (2006.01) |
| *A61K 9/20* | (2006.01) |
| *A61K 45/06* | (2006.01) |
| *A61K 9/14* | (2006.01) |
| *A61K 31/445* | (2006.01) |

(52) U.S. Cl.
CPC .......... *A61K 31/443* (2013.01); *A61K 9/145* (2013.01); *A61K 9/146* (2013.01); *A61K 9/2013* (2013.01); *A61K 9/2072* (2013.01); *A61K 31/192* (2013.01); *A61K 45/06* (2013.01)

(58) Field of Classification Search
None
See application file for complete search history.

(56) References Cited

U.S. PATENT DOCUMENTS

| 6,969,529 B2 * | 11/2005 | Bosch | A61K 9/145 424/451 |
|---|---|---|---|
| 7,495,103 B2 | 2/2009 | Hadida-Ruah | |
| 8,507,534 B2 | 8/2013 | Keshavarz-Shokri | |
| 8,653,103 B2 | 2/2014 | Keshavarz-Shokri | |
| 8,716,338 B2 | 5/2014 | Young | |
| 8,846,718 B2 | 9/2014 | Keshavarz-Shokri | |
| 8,883,206 B2 * | 11/2014 | Dokou | A61K 9/1652 424/465 |
| 8,993,600 B2 | 3/2015 | Hadida Ruah | |
| 2013/0085158 A1 | 4/2013 | Keshavarz-Shokri | |
| 2013/0296379 A1 | 11/2013 | Keshavarz-Shokri | |
| 2014/0163068 A1 | 6/2014 | Verwijs | |
| 2014/0221430 A1 | 8/2014 | Keshavarz-Shokri | |
| 2015/0132388 A1 | 5/2015 | Angi | |
| 2015/0140094 A1 | 5/2015 | Verwijs | |
| 2015/0196539 A1 | 7/2015 | Keshavarz-Shokri | |
| 2016/0039800 A1 | 2/2016 | Young | |

FOREIGN PATENT DOCUMENTS

| WO | 2009076141 | 6/2009 |
|---|---|---|
| WO | 2011127241 | 10/2011 |
| WO | 2011127290 | 10/2011 |
| WO | 2013112804 | 8/2013 |
| WO | 2015071837 | 5/2015 |
| WO | 2015071841 | 5/2015 |
| WO | 2015073231 | 5/2015 |
| WO | 2015121836 | 8/2015 |
| WO | 2015175773 | 11/2015 |

OTHER PUBLICATIONS

Thakur et al., "A Review on Solid Dispersions," World Journal of Pharmacy and Pharmaceutical Sciences, vol. 3, Issue 9, 173-187, Aug. 9, 2014.*
Khatry et al., "Surface Solid Dispersion—A Review," International Journal of Pharmaceutical Sciences and Nanotechnology, vol. 6, Issue 1, Apr.-Jun. 2013.*
Wainright et al., "Lumacaftor-Ivacaftor in Patients with Cystic Fibrosis Homozygous for Phe508del CFTR," NEJM 2015;373:220-231.*
International Application No. PCT/IB2017/052372, International Search Report and Written Opinion of the International Searching Authority, dated Sep. 8, 2017; 11 pages.
Rask, M. et al., "Influence of PVP/VA Copolymer Solubility", European Journal of Pharmaceutical Sciences, 85:10-7, (2016).

(Continued)

*Primary Examiner* — Jared Barsky
(74) *Attorney, Agent, or Firm* — Dennis A. Bennett; Brock D. Levin; Lauren L. Stevens

(57) ABSTRACT

Disclosed herein are pharmaceutically acceptable complex formulations comprising complexes of Lumacaftor, or a salt, or derivative thereof together with complexation agents and, optionally, pharmaceutically acceptable excipients; processes for the preparation thereof and pharmaceutical compositions containing them. The complex formulations have improved dissolution and permeability in fasted and fed state simulation that is expected to deliver full absorption and the elimination of the food effect.

15 Claims, 12 Drawing Sheets

(56) References Cited

OTHER PUBLICATIONS

Rosebraugh, C., "Highlights of Prescribing Information. These highlights do not include all the information needed to use ORKAMBI safely and effectively. See full prescribing information for ORKAMBI", Retrieved from the Internet: https://www.accessdata.fda.gov/drugsatfda_docs/label/2015/206038orig1s000lbl.pdf; (Jul. 1, 2015).

* cited by examiner

Fig. 1

| | | Pharmaceutically acceptable excipient | | | | | | | | | | | | | | | | | | | | | |
|---|---|---|---|---|---|---|---|---|---|---|---|---|---|---|---|---|---|---|---|---|---|---|---|
| | | Beta-cyclodextrin | Citric Acid | Cetylpyridinium chloride | D-Mannitol | Dioctyl sodium sulfosuccinate | Kollicoat-IR | Lactose | Poloxamer (Lutrol F127) | Meglumine | Sodium-Gluconate | Sodium Acetate | NONE | Polyacrylamide | pDADMAC | Poloxamer (Pluronic PE10500) | Polimer-cyclodextrin | Polyvinyl-alcohol | Sulfobutylether-ß-cyclodextrin | Sodium deoxycolate | Sodium-lauryl-sulfate | Solutol HS15 | TPGS | Trehalose |
| Complexation agent | Eudragit EPO | - | + | + | - | - | - | - | - | - | - | - | - | - | - | - | - | - | - | - | - | - | - | - |
| | Gelucire 44/14 | - | - | + | - | + | - | - | + | + | - | + | + | - | - | - | - | + | + | - | - | - | + | - |
| | Gelucire 50/13 | + | + | + | + | - | - | - | - | - | - | - | + | - | - | - | - | - | + | - | - | - | + | - |
| | Hypromellose acetate succiante | - | - | - | - | - | - | - | - | + | - | + | - | - | - | - | - | - | - | - | - | - | - | - |
| | Klucell EF | - | - | - | + | + | + | + | - | + | - | + | + | - | - | - | - | + | + | - | + | - | + | + |
| | Klucell LF | - | - | - | - | + | + | + | - | + | - | + | + | - | - | - | - | + | + | - | + | - | + | + |
| | Poloxamer (Lutrol F127) | - | - | - | - | + | + | - | - | + | + | + | + | - | - | - | - | + | + | + | - | - | + | - |
| | Kollidon VA64 | + | - | + | + | + | + | + | + | + | + | + | + | + | + | - | + | + | + | - | + | - | + | + |
| | PEG2000 | - | - | + | - | - | - | - | - | + | - | + | - | - | - | - | - | - | - | - | - | - | + | - |
| | PEG6000 | - | - | + | - | - | - | - | - | - | - | - | - | - | + | - | - | - | - | - | - | - | + | - |
| | PEOX50 | - | - | + | - | + | - | - | + | - | + | - | - | - | - | - | - | - | - | - | + | - | + | - |
| | PEOX500 | - | - | + | - | + | - | - | + | + | - | + | - | - | - | + | - | + | + | - | + | - | + | - |
| | Plasdone K-12 | - | - | - | - | + | - | - | + | - | + | - | - | - | - | - | - | - | - | - | + | - | - | - |
| | Pluronic PE10500 | - | - | + | - | - | - | - | + | - | + | - | - | + | - | - | + | - | + | - | - | - | + | - |
| | Pluronic PE6800 | - | - | + | - | - | - | - | + | - | + | - | - | - | - | - | - | - | - | + | - | - | - | - |
| | Pluronic F108 | - | - | + | - | + | - | - | + | - | + | - | + | - | - | - | - | + | + | - | - | - | - | - |
| | PMAMVE | - | - | - | - | + | - | + | - | - | - | - | - | - | + | - | - | - | - | - | + | - | + | - |
| | PVP K90 | - | - | + | - | + | - | - | + | - | + | - | - | - | - | - | - | - | - | - | + | - | - | - |
| | PVP 10 | - | - | - | - | + | - | - | + | - | + | - | - | - | - | - | - | - | - | - | + | - | - | - |
| | Tetronic 1107 | + | - | + | + | + | - | - | + | - | + | - | - | - | - | - | - | - | + | + | + | - | + | - |
| | TPGS | - | + | + | - | - | - | - | + | - | + | - | - | + | - | - | + | + | + | - | - | - | + | - |
| | PVP 40 | - | - | - | - | - | - | - | + | - | + | - | - | + | - | - | - | - | - | - | + | - | - | - |
| | Soluplus | - | - | - | - | + | - | - | - | + | - | + | - | - | - | - | - | - | - | - | + | - | - | - |

\+ redispersable solid Lumacaftor complex in ultrapurified water
\- non-redispersable solid Lumacaftor complex in ultrapurified water

Fig. 2

| Complexation agent | Pharmaceutically acceptable excipient | Redispersibility | PAMPA permeability ($*10^{-6}$ cm/s) |
|---|---|---|---|
| Kollidon VA 64 | Sodium lauryl sulfate | + | 2.54 |
| Kollidon VA 64 | Polyvinyl-alcohol | - | 2.28 |
| Plasdone K-12 | Sodium acetate | - | 2.06 |
| Lutrol F127 | Sodium acetate | + | 1.94 |
| TPGS | Sodium acetate | + | 1.86 |
| PVP K-90 | Sodium lauryl sulfate | - | 1.72 |
| TPGS | Citric Acid | - | 1.54 |
| Kollidon VA 64 | Sodium acetate | + | 1.49 |
| PVP 10 | Sodium lauryl sulfate | - | 1.48 |
| Soluplus | Sodium acetate | - | 1.44 |
| Lutrol F108 | Sodium acetate | + | 1.24 |
| PVP K-90 | Sodium acetate | - | 1.24 |
| TPGS | Sodium acetate | + | 1.23 |
| Kollidon VA 64 | SBECD | + | 1.18 |
| Kollidon VA 64 | PDADMAC | - | 0.78 |
| Lutrol F127 | Meglumine | - | 0.66 |
| Pluronic PE 6800 | Meglumine | - | 0.64 |
| Soluplus | Meglumine | - | 0.61 |
| Kollidon VA 64 | Meglumine | + | 0.59 |
| TPGS | Meglumine | + | 0.53 |
| TPGS | Meglumine | + | 0.48 |
| *Crystalline API* | | - | *0.58* |

*Mass ratio of API:complexation agent:pharmaceutically acceptable excipient = 1:2:1*

Fig. 4

| Flow rate | | Temperature | Particle size (nm) measured by DLS 'as synthesized' | |
|---|---|---|---|---|
| Solution 1 (mL/min) | Solution 2 (mL/min) | (°C) | d(50) | d(90) |
| 1 | 4 | 25 | Inhomogenous solution | |
| 2 | 8 | 25 | 284 | 484 |
| 3 | 12 | 25 | 270.7 | 379 |
| 5 | 20 | 25 | 269.8 | 354 |
| 7.5 | 30 | 25 | 169.4 | 252.3 |
| 10 | 40 | 25 | 150.5 | 195.4 |

Fig. 11

| Composition | Lumacaftor content of the dispersions (mg/mL) | Apparent solubility (mg/mL) |
|---|---|---|
| Crystalline Lumacaftor | 1 | 0 |
| Physical mixture | 1 | 0.032 |
| Ball milled Lumacaftor | 1 | 0.003 |
| Ball milled Lumacaftor with Kollidon VA64 and SDS | 1 | 0.125 |
| Complex Lumacaftor | 1 | 0.950 |
| Complex Lumacaftor | 20 | 14.913 |

Fig. 12

| Composition | PAMPA permeability ($\times 10^{-6}$ cm/s) |
|---|---|
| Crystalline Lumacaftor | 0.344 |
| Physical mixture | 0.226 |
| Ball milled Lumacaftor | 0.288 |
| Ball milled Lumacaftor with Kollidon VA64 and SDS | 1.200 |
| Complex Lumacaftor formulation | 4.651 |

COMPLEXES OF LUMACAFTOR AND ITS SALTS AND DERIVATIVES, PROCESS FOR THE PREPARATION THEREOF AND PHARMACEUTICAL COMPOSITIONS CONTAINING THEM

This application claims the benefit of priority to U.S. provisional application No. 62/327,148, filed Apr. 25, 2016, the disclosure of which is hereby incorporated by reference as if written herein in its entirety.

FIELD OF THE INVENTION

Disclosed herein are stable complexes with controlled particle size, increased apparent solubility and increased dissolution rate comprising as active compound Lumacaftor, or its salts, or derivatives thereof, which is useful in the treatment of cystic fibrosis transmembrane conductance regulator (CFTR) mediated disease. More specifically, the complexes possess instantaneous redispersibility, increased apparent solubility and permeability in fasted and fed state simulation that is expected to deliver full absorption and eliminate the food effect. Further disclosed are methods of formulating and manufacturing complexes, pharmaceutical compositions containing said complexes, and methods of treatment using the complex and its compositions.

BACKGROUND OF THE INVENTION

Lumacaftor is one of the active ingredients in ORKAMBI® tablets, which has the following chemical name: 3-[6-({[1-(2,2-difluoro-1,3-benzodioxo-5-yl)cyclopropyl]carbonyl}amino)-3-methylpyridin-2-yl]benzoic acid. The molecular formula for lumacaftor is $C_{24}H_{18}F_2N_2O_5$. The molecular weight for Lumacaftor is 452.41. The structural formula is:

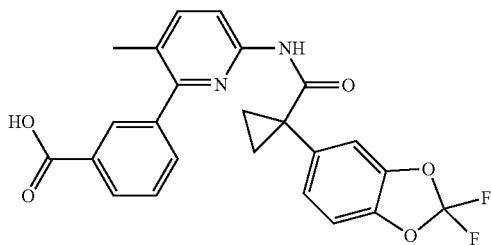 [SMILES: Cc1ccc(NC(=O)C2(c3ccc4c(c3)OC(F)(F)O4)CC2)nc1-c1cccc(C(=O)O)c1]

Lumacaftor is a white to off-white powder that is practically insoluble in water (0.02 mg/mL).

ORKAMBI® is available as a pink, oval-shaped, film-coated tablet for oral administration containing 200 mg of Lumacaftor and 125 mg of Ivacaftor. Each ORKAMBI® tablet contains 200 mg of Lumacaftor and 125 mg of Ivacaftor, and the following inactive ingredients: microcrystalline cellulose; croscarmellose sodium; hypromellose acetate succinate; magnesium stearate; povidone; and sodium lauryl sulfate. The tablet film coat contains carmine, FD&C Blue #1, FD&C Blue #2, polyethylene glycol, polyvinyl alcohol, talc, and titanium dioxide. The printing ink contains ammonium hydroxide, iron oxide black, propylene glycol, and shellac.

Lumacaftor improves the conformational stability of F508del-CFTR, resulting in increased processing and trafficking of mature protein to the cell surface. In-vitro studies have demonstrated that Lumacaftor acts directly on the CFTR protein in primary human bronchial epithelial cultures and other cell lines harboring the F508del-CFTR mutation to increase the quantity, stability, and function of F508del-CFTR at the cell surface, resulting in increased chloride ion transport.

Following multiple oral dose administrations of Lumacaftor, the exposure of Lumacaftor increased roughly proportionally with dose from 50 to 1000 mg qd. In subjects with cystic fibrosis (CF), the Lumacaftor $C_{max}$ and AUC also increases approximately proportional with the dose over the Lumacaftor 25 mg qd to 400 mg q12h dose range. The exposure of Lumacaftor increased approximately 1.6-to 2.0-fold when given with fat containing food. The median (range) time of the maximum concentration ($t_{max}$) is approximately 4.0 (2.0, 9.0) hours in the fed state.

When a single dose of Lumacaftor and Ivacaftor was administered with fat-containing foods, Lumacaftor exposure was approximately 2 times higher and Ivacaftor exposure was approximately 3 times higher than when taken in a fasting state.

Following multiple oral dose administration of Lumacaftor in combination with Ivacaftor, the exposure of Lumacaftor generally increased proportional to dose over the range of 200 mg every 24 hours to 400 mg every 12 hours. The median (range) $t_{max}$ of Lumacaftor is approximately 4.0 hours (2.0; 9.0) in the fed state.

Lumacaftor is approximately 99% bound to plasma proteins, primarily to albumin. After oral administration of 200 mg every 24 hours for 28 days to patients with CF in a fed state, the mean (±SD) for apparent volumes of distribution was 86.0 (69.8) L.

The half-life of Lumacaftor is approximately 26 hours in patients with CF. The typical apparent clearance, CL/F (CV), of Lumacaftor was estimated to be 2 38 L/hr (29.4%) for patients with CF.

Lumacaftor is not extensively metabolized in humans with the majority (51%) of Lumacaftor excreted unchanged in the feces. There was minimal elimination of Lumacaftor and its metabolites in urine (only 8.6% of total radioactivity was recovered in the urine with 0.18% as unchanged parent). In-vitro and in vivo data indicate that Lumacaftor is mainly metabolized via oxidation and glucuronidation.

Lumacaftor has low aqueous solubility and high permeability assessed via the colorectal adenocarcinoma (Caco-2) cell system. Although pH-dependent solubility was observed, the Lumacaftor drug substance is practically insoluble in water and buffer solutions of pH 1.0 to pH 8.0. Therefore, Lumacaftor is suggested to be a BCS Class 2 (low solubility/high permeability) compound.

Since Lumacaftor is considered a BCS class II, the drug substance was jet-milled early in development to reduce the particle size and potentially improve bioavailability. Based on these studies a control on Lumacaftor particle size in the drug substance specification was established.

Various formulations have been used in the development of Lumacaftor alone and in combination which includes suspension, capsules and tablets. Comparative exposure of the different formulations of Lumacaftor was seen in single dose studies in healthy volunteers. Exposure of the suspension is lower than that seen for capsules and tablets. Early clinical studies were conducted with the co-administration of both Ivacaftor and Lumacaftor. A cross-over study (007) was conducted to evaluate the relative bioavailability of the fixed dose combination tablet as compared to the separate tablets. The tablet and FDC appear to be bioequivalent, and the only parameter that did not meet standard bioequivalence criteria is the $C_{max}$ of Ivacaftor (GLSMR [90% CI]-

1.20 [1.09, 1.33]). However, for practical purposes, this is acceptable and the PK results from tablet formulation can be considered applicable to the FDC as well.

The main medical concerns surrounding Lumacaftor is the 2-fold positive food effect when the drug is taken with a high fat meal. Elimination of the food effect would allow the administration of the drug on an empty stomach and more reliable plasma concentrations.

In order to overcome the problems associated with prior conventional Lumacaftor formulations and available drug delivery systems, novel complex formulations of Lumacaftor and salts or derivatives thereof together with complexation agents and pharmaceutically acceptable excipients were prepared. Novel complex formulations of the present invention are characterized by instantaneous redispersibility, increased apparent solubility, instantaneous dissolution, increased apparent permeability in fasted and fed state simulation that is expected to deliver full absorption and the elimination of the food effect.

BRIEF DESCRIPTION OF THE INVENTION

Disclosed herein is a stable complex with improved physicochemical characteristics and enhanced biological performance comprising
  i. Lumacaftor, or a salt or derivative thereof;
  ii. at least one complexation agent chosen from polyethylene glycol glycerides composed of mono-, di- and triglycerides and mono- and diesters of polyethylene glycol, hydroxypropylcellulose, poloxamers (copolymers of ethylene oxide and propylene oxide blocks), copolymer of vinylpyrrolidone and vinyl acetate, poly (2-ethyl-2-oxazoline), polyvinylpyrrolidone, poly(maleic acid/methyl vinyl ether), (polyvinyl caprolactam-polyvinyl acetate-polyethylene glycol graft copolymer, polyoxyl 15 hydroxystearate, ethylene oxide/propylene oxide tetra functional block copolymer, and d-alpha tocopheryl polyethylene glycol 1000 succinate; and
  iii. optionally, one or more pharmaceutically acceptable excipients;
wherein said complex has a particle size is between 10 nm and 500 nm, and possesses one or more among the following features:
  a) is instantaneously redispersable in physiological relevant media;
  b) is stable in solid form and in colloid solution and/or dispersion;
  c) has an apparent solubility in water of at least 1 mg/mL;
  d) has a PAMPA permeability of at least $2 \times 10^{-6}$ cm/s when dispersed in FaSSIF or FeSSIF biorelevant media, which does not decrease in time at least for 12 months.

In an embodiment, said complex has a particle size in the range between 10 nm and 250 nm.

In an embodiment, said complex exhibits X-ray amorphous character in the solid form.

In an embodiment, said complex possesses at least two of the properties described in a)-d).

In an embodiment, said complex possesses at least three of the properties described in a)-d).

In an embodiment, said complex possesses instantaneous redispersibility, has an apparent solubility in water of at least 1 mg/mL, improved permeability in fasted and fed state simulation, exhibits no observable food effect which deliver full absorption and the opportunity of precise dosing and ease of administration of the reconstituted complex Lumacaftor in solution form.

In an embodiment, said complex possesses instantaneous redispersibility, has a PAMPA permeability of at least $2 \times 10^{-6}$ cm/s when dispersed in, FaSSIF or FeSSIF biorelevant media, which does not decrease in time at least for 1 month, exhibits no observable food effect which deliver the opportunity of precise dosing and ease of administration of the reconstituted complex Lumacaftor in solution form.

In an embodiment, said complex has an apparent solubility in water of at least 1 mg/mL and a PAMPA permeability of at least $2 \times 10^{-6}$ cm/s in FaSSIF and FeSSIF biorelevant media.

In an embodiment, said complex possesses instantaneous redispersibility, has an apparent solubility in water of at least 1 mg/mL, and has a PAMPA permeability of at least $2 \times 10^{-6}$ cm/s in FaSSIF and FeSSIF biorelevant media.

In an embodiment, said complexing agent is a copolymer of vinylpyrrolidone and vinylacetate.

In an embodiment, said pharmaceutically acceptable excipient is chosen from sodium deoxycholate, dioctyl sodium sulfosuccinate, sodium acetate, cetylpyridinium chloride, citric acid, meglumine and sodium lauryl sulfate.

In an embodiment, said pharmaceutically acceptable excipient is sodium lauryl sulfate.

In an embodiment, said complex comprises
  a) Lumacaftor;
  b) a complexation agent that is a copolymer of vinylpyrrolidone and vinylacetate;
  c) an excipient that is sodium lauryl sulfate;
  wherein said complex is characterized by infrared (ATR) peaks at 635 cm$^{-1}$, 703 cm$^{-1}$, 747 cm$^{-1}$, 837 cm$^{-1}$, 1021 cm$^{-1}$, 1165 cm$^{-1}$, 1231 cm$^{-1}$, 1288 cm$^{-1}$, 1369 cm$^{-1}$, 1423 cm$^{-1}$, 1462 cm$^{-1}$, 1494 cm$^{-1}$, 1667 cm$^{-1}$ and 1731 cm$^{-1}$; and
  is characterized by Raman shifts at 553 cm$^{-1}$, 602 cm$^{-1}$, 635 cm$^{-1}$, 654 cm$^{-1}$, 747 cm$^{-1}$, 841 cm$^{-1}$, 899 cm$^{-1}$, 934 cm$^{-1}$, 1002 cm$^{-1}$, 1021 cm$^{-1}$, 1117 cm$^{-1}$, 1205 cm$^{-1}$, 1232 cm$^{-1}$, 1310 cm$^{-1}$, 1352 cm$^1$, 1372 cm$^{-1}$, 1428 cm$^{-1}$, 1444 cm$^{-1}$, 1497 cm$^{-1}$, 1592 cm$^{-1}$, 1609 cm$^{-1}$, 1677 cm$^{-1}$ and 1737 cm$^{-1}$.

In an embodiment, said complex comprises a complexation agent which is a copolymer of vinylpyrrolidone and vinylacetate and pharmaceutically acceptable excipient which is sodium lauryl sulfate, are present in a total amount ranging from about 1.0 weight % to about 95.0 weight % based on the total weight of the complex.

In an embodiment, said complex comprises a complexing agent which is a copolymer of vinylpyrrolidone and vinylacetate and pharmaceutically acceptable excipient which is sodium lauryl sulfate, are present in a total amount ranging from about 50 weight % to about 95.0 weight % based on the total weight of the complex.

In an embodiment, said complex has an increased dissolution rate.

Disclosed herein is a process for the preparation of said stable complex, said process comprising the step of mixing a pharmaceutically acceptable solution containing Lumacaftor, and at least one complexing agent which is copolymers of vinylpyrrolidone and vinylacetate with an aqueous solution containing at least one pharmaceutically accepted excipient selected from the group of sodium deoxycholate, dioctyl sodium sulfosuccinate, sodium acetate, cetylpyridinium chloride, citric acid, meglumine and sodium lauryl sulfate.

In an embodiment, said process is performed in a continuous flow instrument.

In an embodiment, said continuous flow instrument is a microfluidic flow instrument.

In an embodiment, said pharmaceutically acceptable solvent of said pharmaceutically acceptable solution is chosen from methanol, ethanol, isopropanol, n-propanol, acetone, acetonitrile, dimethyl-sulfoxide, tetrahydrofuran, or combinations thereof.

In an embodiment, said pharmaceutically acceptable solvent is methanol.

In an embodiment, said pharmaceutically acceptable solution and said aqueous solution are miscible with each other and the aqueous solution comprises 0.1 to 99.9% weight of the final solution.

Disclosed herein is a pharmaceutical composition comprising said stable complex together with a pharmaceutically acceptable carrier.

In an embodiment, said composition is suitable for oral, pulmonary, rectal, colonic, parenteral, intracisternal, intravaginal, intraperitoneal, ocular, otic, local, buccal, nasal, or topical administration.

In an embodiment, said composition is suitable for oral administration.

In an embodiment, said composition comprises fast dissolving granules of the complex formulation.

In an embodiment, said granules are suitable for the preparation of sachet dosage form.

Disclosed herein is said complex for use in the treatment of CFTR mediated diseases.

In an embodiment, said CFTR mediated disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

Disclosed herein is a method of treatment of CFTR mediated diseases comprising administration of a therapeutically effective amount of said complex or said pharmaceutical composition.

Disclosed herein is a stable complex comprising
a) 5-40% by weight of Lumacaftor, or a salt thereof;
b) 50-90% by weight of a copolymer of vinylpyrrolidone and vinylacetate; and
c) 0.01-50% by weight of sodium lauryl sulfate
wherein said complex has a controlled particle size in the range between 10 nm and 500 nm; and
wherein said complex is not obtained via a milling process, high pressure homogenization process, encapsulation process or solid dispersion processes.

In an embodiment, said complex further comprises one or more additional active agents.

In an embodiment, said additional active agent Ivacaftor, Tezacaftor or chosen from agents used for the treatment of CFTR mediated diseases.

DESCRIPTION OF THE INVENTION

Disclosed herein are stable complexes comprising as active compound Lumacaftor, or salts or derivatives thereof; and at least one complexation agent.

In an embodiment, said complex further comprises at least one pharmaceutically acceptable excipient.

We have found that only the selected combinations of complexation agents and pharmaceutically acceptable excipients result in stable complex formulations having improved physicochemical characteristics and enhanced biological performance compared to crystalline, lumacaftor and/or ORKAMBI®.

The complexing agents themselves or together with the pharmaceutically acceptable excipients have the function to form a complex structure with an active pharmaceutical ingredient through non-covalent secondary interactions. The secondary interactions can form through electrostatic interactions such as ionic interactions, H-bonding, dipole-dipole interactions, dipole-induced dipole interactions, London dispersion forces, π-π interactions, and hydrophobic interactions.

In an embodiment, said complex has improved physicochemical characteristics and enhanced biological performance comprising
  i. Lumacaftor, or a salt thereof;
  ii. at least one complexation agent chosen from polyethylene glycol glycerides composed of mono-, di- and triglycerides and mono- and diesters of polyethylene glycol, hydroxypropylcellulose, poloxamers (copolymers of ethylene oxide and propylene oxide blocks), copolymer of vinylpyrrolidone and vinyl acetate, poly(2-ethyl-2-oxazoline), polyvinylpyrrolidone, poly(maleic acid/methyl vinyl ether), (polyvinyl caprolactam-polyvinyl acetate-polyethylene glycol graft copolymer, polyoxyl 15 hydroxystearate, ethylene oxide/propylene oxide tetra functional block copolymer, and d-alpha tocopheryl polyethylene glycol 1000 succinate; and
  iii. optionally, pharmaceutically acceptable excipients;
wherein said complex has a particle size is between 10 nm and 500 nm, and possesses one or more among the following features:
  a) is instantaneously redispersable in physiological relevant media;
  b) is stable in solid form and in colloid solution and/or dispersion;

c) has an apparent solubility in water of at least 1 mg/mL; and d) has a PAMPA permeability of at least $2 \times 10^{-6}$ cm/s when dispersed in FaSSIF or FeSSIF biorelevant media, which does not decrease in time at least for 12 month.

In an embodiment, said complexation agent is chosen from polyethylene glycol glycerides composed of mono-, di- and triglycerides and mono- and diesters of polyethylene glycol, hydroxypropylcellulose, poloxamers (copolymers of ethylene oxide and propylene oxide blocks), copolymer of vinylpyrrolidone and vinyl acetate, poly(2-ethyl-2-oxazoline), polyvinylpyrrolidone, poly(maleic acid/methyl vinyl ether), (polyvinyl caprolactam-polyvinyl acetate-polyethylene glycol graft copolymer, polyoxyl 15 hydroxystearate, ethylene oxide/propylene oxide tetra functional block copolymer, and d-alpha tocopheryl polyethylene glycol 1000 succinate, polyethylene-glycols.

In an embodiment, said complexation agent is copolymer of vinylpyrrolidone and vinyl acetate.

In an embodiment, said copolymer of vinylpyrrolidone and vinyl acetate has a 60:40 weight ratio of vinylpyrrolidone:vinyl acetate monomers.

In an embodiment, said pharmaceutically acceptable excipient is chosen from sodium lauryl sulfate (SDS), dioctyl sodium sulfosuccinate (DSS), cetylpyridinium chloride (CPC), sodium acetate (NaOAC), sodium deoxycholate (SDC), meglumine, D-mannitol, Kollicoat-IR, citric acid, and lactose.

In an embodiment, said pharmaceutically acceptable excipient is chosen from sodium deoxycholate, dioctyl sodium sulfosuccinate, sodium acetate, cetylpyridinium chloride, citric acid, meglumine and sodium lauryl sulfate.

In an embodiment, said pharmaceutically acceptable excipient is sodium lauryl sulfate.

In some embodiments, the compositions may additionally include one or more pharmaceutically acceptable excipients, auxiliary materials, carriers, active agents or combinations thereof.

In an embodiment, said particle size is between 10 nm and 250 nm.

In an embodiment, said complex has increased dissolution rate compared to crystalline Lumacaftor.

In an embodiment, said complex is stable in solid form and in colloid solution and/or dispersion.

In an embodiment, said complex has apparent solubility in water is at least 1 mg/mL.

In an embodiment, said complex exhibits X-ray amorphous character in the solid form.

In an embodiment, said complex has a PAMPA permeability of at least $2 \times 10^{-6}$ cm/s when dispersed in FaSSIF media, which does not decrease in time at least for 12 months.

In an embodiment, the variability of exposure of the complex is significantly reduced compared to the commercially available form (ORKAMBI®).

In an embodiment, said complex has no observable food effect in-vitro, which allows the opportunity of precise dosing and ease of administration of the reconstituted complex in solution form.

In an embodiment said complex or its pharmaceutical composition characterized by Raman spectrum shown in FIG. 7 and ATR spectrum shown in FIG. 8.

In an embodiment said complex is characterized by Raman shifts at 553 cm$^{-1}$, 602 cm$^{-1}$, 635 cm$^{-1}$, 654 cm$^{-1}$, 747 cm$^{-1}$, 841 cm$^{-1}$, 899 cm$^{-1}$, 934 cm$^{-1}$, 1002 cm$^{-1}$, 1021 cm$^{-1}$, 1117 cm$^{-1}$, 1205 cm$^{-1}$, 1232 cm$^{-1}$, 1310 cm$^{-1}$, 1352 cm$^{-1}$, 1372 cm$^{-1}$, 1428 cm$^{-1}$, 1444 cm$^{-1}$, 1497 cm$^{-1}$, 1592 cm$^{-1}$, 1609 cm$^{-1}$, 1677 cm$^{-1}$ and 1737 cm$^{-1}$.

In an embodiment said complex is characterized by infrared (ATR) peaks at 635 cm$^{-1}$, 703 cm$^{-1}$, 747 cm$^{-1}$, 837 cm$^{-1}$, 1021 cm$^{-1}$, 1165 cm$^{-1}$, 1231 cm$^{-1}$, 1288 cm$^{-1}$, 1369 cm$^{-1}$, 1423 cm$^{-1}$, 1462 cm$^{-1}$, 1494 cm$^{-1}$, 1667 cm$^{-1}$ and 1731 cm$^{-1}$.

In an embodiment said complex comprises
a) Lumacaftor; or a combination of active compounds including Lumacaftor;
b) a complexing agent which is copolymer of vinylpyrrolidone and vinyl acetate; and
c) sodium lauryl sulfate as an excipient.

In an embodiment, said complex comprises complexation agent which is a copolymer of vinylpyrrolidone and vinylacetate and a pharmaceutically acceptable excipient which is sodium lauryl sulfate, in a total amount ranging from about 1.0 weight % to about 95.0 weight % based on the total weight of the complex.

In an embodiment, said complex comprises complexation agent which is copolymer of vinylpyrrolidone and vinylacetate and pharmaceutically acceptable excipient which is sodium lauryl sulfate comprise 50 weight % to about 95 weight % of the total weight of the complex.

Further disclosed herein is a stable complex comprising
i. 5-40% by weight of Lumacaftor, its salt, or derivatives thereof;
ii. 50-90% by weight of copolymer of vinylpyrrolidone and vinylacetate;
iii. 0.01-30% by weight of sodium lauryl sulfate.

Disclosed herein is a process for the preparation of a stable complex of Lumacaftor, said process comprising the step of mixing a pharmaceutically acceptable solution containing the active agent and at least one complexing agent and optionally one or more pharmaceutically acceptable excipient with an aqueous solution containing optionally least one pharmaceutically acceptable excipient.

In an embodiment said complex is obtained via a mixing process.

In an embodiment said complex is obtained via a continuous flow mixing process.

In an embodiment said process is performed in a continuous flow instrument.

In an embodiment said continuous flow instrument is a microfluidic flow instrument.

In an embodiment, said complex is not obtained via a milling process, high pressure homogenization process, encapsulation process and solid dispersion processes.

In an embodiment, the pharmaceutically acceptable solvent of said pharmaceutically acceptable solution is chosen from methanol, ethanol, 1-propanol, 2-propanol, acetone, acetonitrile, dimethyl-sulfoxide, tetrahydrofuran, methylethyl ketone or combinations thereof.

In an embodiment, said pharmaceutically acceptable solvent is methanol.

In an embodiment, said pharmaceutically acceptable solution and said aqueous solution are miscible with each other.

In an embodiment, said aqueous solution comprises 0.1 to 99.9% weight of the final solution.

In an embodiment, said aqueous solution comprises 50 to 90% weight of the final solution.

In an embodiment, said aqueous solution comprises 50 to 80% weight of the final solution.

In an embodiment, said aqueous solution comprises 50 to 70% weight of the final solution.

In an embodiment, said aqueous solution comprises 50 to 60% weight of the final solution.

In an embodiment, said aqueous solution comprises 45 to 55% weight of the final solution.

In an embodiment, said aqueous solution comprises 50% weight of the final solution.

In an embodiment, said aqueous solution comprises 35 to 45% weight of the final solution.

In an embodiment, said aqueous solution comprises 25 to 35% weight of the final solution.

In an embodiment, said aqueous solution comprises 15 to 25% weight of the final solution.

In an embodiment, said aqueous solution comprises 5 to 15% weight of the final solution.

In an embodiment, a pharmaceutical composition comprising the complex together with pharmaceutically acceptable carriers.

In an embodiment, said pharmaceutical composition is suitable for oral, pulmonary, rectal, colonic, parenteral, intracisternal, intravaginal, intraperitoneal, ocular, otic, local, buccal, nasal, or topical administration.

In an embodiment, said pharmaceutical compositions are suitable for oral administration.

In an embodiment, said pharmaceutical composition comprises fast dissolving granules.

In an embodiment, said granules are suitable for the preparation of sachet dosage form.

In an embodiment, said complexes are for use in the manufacture of a medicament for the treatment of CFTR mediated diseases.

In an embodiment, said complexes are used for the treatment of CFTR mediated diseases.

CFTR mediated disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

In an embodiment, a method of treatment of CFTR mediated diseases comprises administration of a therapeutically effective amount of complexes or pharmaceutical compositions as described herein.

In an embodiment, a method for reducing the therapeutically effective dosage of Lumacaftor compared to commercially available ORKAMBI® comprises oral administration of a pharmaceutical composition as described herein.

In an embodiment, said complexes further comprise one or more additional active agents.

In an embodiment, said additional active agent is Ivacaftor, Tezacaftor or chosen from agents used for the treatment of CFTR mediated diseases.

In an embodiment said complex comprises Lumacaftor; or a combination of active compounds including Lumacaftor; a complexing agent which is copolymers of vinylpyrrolidone and vinyl acetate and sodium lauryl sulfate as an excipient; said complexes characterized in that they possess at least one of the following properties:

a) is instantaneously redispersable in physiological relevant media;

b) is stable in solid form and in colloid solution and/or dispersion;

c) has apparent solubility in water of at least 1 mg/mL; and d) has a PAMPA permeability of at least $2\times10^{-6}$ cm/s when dispersed in FaSSIF or FeSSIF biorelevant media, which does not decrease in time at least for 12 month.

In an embodiment, said complex possesses at least two of the properties described in a)-d).

In an embodiment, said complex possesses at least three of the properties described in a)-d).

The novel complexes of the present invention possess instantaneous redispersibility, increased apparent solubility and permeability in fasted and fed state simulation that is expected to deliver full absorption and eliminate the food effect which deliver the opportunity of precise dosing and ease of administration of the reconstituted complex in solution form.

The expression Lumacaftor is generally used for Lumacaftor, or its salts or its derivatives.

In an embodiment, said complexation agent is chosen from polyethylene glycol glycerides composed of mono-, di- and triglycerides and mono- and diesters of polyethylene glycol, hydroxypropylcellulose, poloxamers (copolymers of ethylene oxide and propylene oxide blocks), copolymer of vinylpyrrolidone and vinyl acetate, poly(2-ethyl-2-oxazoline), polyvinylpyrrolidone, poly(maleic acid/methyl vinyl ether), (polyvinyl caprolactam-polyvinyl acetate-polyethylene glycol graft copolymer, polyoxyl 15 hydroxystearate, ethylene oxide/propylene oxide tetra functional block copolymer, and d-alpha tocopheryl polyethylene glycol 1000 succinate.

In an embodiment, said complexation agent is a copolymer of vinylpyrrolidone and vinyl acetate and said pharmaceutically acceptable excipient is sodium lauryl sulfate, and a) is characterized by Raman shifts at 553 $cm^{-1}$, 602 $cm^{-1}$, 635 $cm^{-1}$, 654 $cm^{-1}$, 747 $cm^{-1}$, 841 $cm^{-1}$, 899 $cm^{-1}$, 934 $cm^{-1}$, 1002 $cm^{-1}$, 1021 $cm^{-1}$, 1117 $cm^{-1}$, 1205 $cm^{-1}$, 1232 $cm^{-1}$, 1310 $cm^{-1}$, 1352 $cm^{-1}$, 1372 $cm^{-1}$, 1428 $cm^{-1}$, 1444 $cm^{-1}$, 1497 $cm^{-1}$, 1592 $cm^{-1}$, 1609 $cm^{-1}$, 1677 $cm^{-1}$ and 1737 $cm^{-1}$; and b) is characterized by infrared (ATR) peaks at 635 cm$^{-1}$, 703 cm$^{-1}$, 747 cm$^{-1}$, 837 cm$^{-1}$, 1021 cm$^{-1}$, 1165 cm$^{-1}$, 1231 cm$^{-1}$, 1288 cm$^{-1}$, 1369 cm$^{-1}$, 1423 cm$^{-1}$, 1462 cm$^{-1}$, 1494 cm$^{-1}$, 1667 cm$^{-1}$ and 1731 cm$^{-1}$.

In some embodiments, the compositions may additionally include one or more pharmaceutically acceptable excipients, auxiliary materials, carriers, active agents or combinations thereof. In some embodiments, active agents may include agents useful for the treatment of CFTR mediated diseases.

Another aspect of the invention is the complex formulations of the Lumacaftor with complexation agents and pharmaceutically acceptable excipients in which the complexation agents and pharmaceutically acceptable excipients preferably are associated or interacted with the Lumacaftor, such as the results of a mixing process or a continuous flow mixing process. In some embodiment, the structure of the complex Lumacaftor formulation is different from the core-shell type milled particle, precipitated encapsulated particles, micelles and solid dispersions.

The pharmaceutical composition of the invention can be formulated: (a) for administration selected from the group consisting of oral, pulmonary, rectal, colonic, parenteral, intracisternal, intravaginal, intraperitoneal, ocular, otic, local, buccal, nasal, and topical administration; (b) into a dosage form selected from the group consisting of liquid dispersions, gels, aerosols, ointments, creams, lyophilized formulations, tablets, capsules; (c) into a dosage form selected from the group consisting of controlled release formulations, fast melt formulations, delayed release formulations, extended release formulations, pulsatile release formulations, and mixed immediate release and controlled release formulations; or (d) any combination of (a), (b), and (c).

The compositions can be formulated by adding different types of pharmaceutically acceptable excipients for oral administration in solid, liquid, local (powders, ointments or drops), or topical administration, and the like.

In an embodiment, the dosage form of the invention is a solid dosage form, although any pharmaceutically acceptable dosage form can be utilized.

Solid dosage forms for oral administration include, but are not limited to, capsules, tablets, pills, powders (sachet), and granules. In such solid dosage forms, the complex formulation of Lumacaftor is admixed with at least one of the following: one or more inert excipients (or carriers): (a) fillers or extenders, such as, lactose, sucrose, glucose, mannitol, sorbitol, dextrose, dextrates, dextrin, erythritol, fructose, isomalt, lactitol, maltitol, maltose, maltodextrin, trehalose, xylitol, starches, microcrystalline cellulose, dicalcium phosphate, calcium carbonate, magnesium carbonate, magnesium oxide; (b) sweetening, flavoring, aromatizing and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid; (c) binders, such as cellulose derivatives, acrylic acid derivatives, alginates, gelatin, polyvinylpyrrolidone, starch derivatives, dextrose, dextrates, dextrin, maltose, maltodextrin; (d) disintegrating agents, such as crospovidon, effervescent compositions, croscarmellose sodium and other cellulose derivatives, sodium starch glycolate and other starch derivatives, alginic acid, certain complex silicates and sodium carbonate; (e) solution retarders, such as acrylates, cellulose derivatives, paraffin; (f) absorption accelerators, such as quaternary ammonium compounds; (g) wetting agents, such as polysorbates, cetyl alcohol and glycerol monostearate; (h) lubricants such as talc, stearic acid and its derivatives, solid polyethylene glycols, sodium lauryl sulfate, glyceryl behenate, medium-chain triglycerides or mixtures thereof. For capsules, tablets, and pills, the dosage forms may also comprise buffering agents.

In an embodiment, the dosage form of the invention is liquid dispersible granules in a sachet form.

In an embodiment, said liquid dispersible granules comprise the complex formulation of Lumacaftor of the present invention together with pharmaceutically acceptable excipients selected from the group of fillers or extenders, such as, lactose, sucrose, glucose, mannitol, sorbitol, dextrose, dextrates, dextrin, erythritol, fructose, isomalt, lactitol, maltitol, maltose, maltodextrin, trehalose, xylitol, starches, microcrystalline cellulose, dicalcium phosphate, calcium carbonate, magnesium carbonate, magnesium oxide.

In an embodiment, said liquid dispersible granules comprise the complex formulation of Lumacaftor of the present invention together with pharmaceutically acceptable excipients selected from the group of sweetening, flavoring, aromatizing and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid.

Further disclosed herein is a liquid dispersible granule composition comprising
  a) 25-95% stable complex formulation of Lumacaftor of the present invention;
  b) 5-75% fillers or extenders;
  c) 0.5-25% binders;
  d) 0.1-5% sweetening, flavoring, aromatizing and perfuming agents;
wherein said liquid dispersible granules disperses within 3 min in liquid; and wherein said liquid dispersible granules obtained by wet or dry processes.

In an embodiment, said dispersion time is between 0.1 min and 10 min.

In an embodiment, said dispersion time is between 0.1 min and 5 min.

In an embodiment, said dispersion time is between 0.1 min and 3 min.

In an embodiment, said dispersion time is between 0.1 min and 1 min.

In an embodiment, said dispersion time is between 0.1 min and 1 min.

In an embodiment, Hausner-ratio of the said liquid dispersible granules of complex Lumacaftor formulations is less than 1.25 more preferably 1.00-1.18

In an embodiment, Hausner-ratio of the said liquid dispersible granules of complex Lumacaftor formulations is between 1.00 and 1.18.

In an embodiment, the particle size (D(90)) of said solid aggregates of complex Lumacaftor formulations is less than 2000 micrometers.

In an embodiment, 60-99% of the said solid aggregates of complex Lumacaftor formulations are in the size range of 160-1200 micrometers In an embodiment, said liquid is water, saliva, other physiologically or biologically acceptable fluid.

In an embodiment, the dosage form is chosen from a tablet and a capsule.

Advantages of the complex Lumacaftor formulation of the invention include, but are not limited to (1) physical and chemical stability, (2) instantaneous redispersibility, (3) stability in colloid solution or dispersion in the therapeutic time window, (4) increased apparent solubility and permeability compared to the conventional Lumacaftor formulation in fasted and fed state simulation that is expected to deliver full absorption and the elimination of the food effect, (5) good processability.

In an embodiment, said complex possesses instantaneous redispersibility, has an apparent solubility in water of at least 1 mg/mL, improved permeability in fasted and fed state simulation, exhibits no observable food effect which deliver full absorption and the opportunity of precise dosing and ease of administration of the reconstituted complex Lumacaftor in solution form.

In an embodiment, said complex possesses instantaneous redispersibility, has a PAMPA permeability of at least $2 \times 10^{-6}$ cm/s when dispersed in, FaSSIF or FeSSIF biorelevant media, which does not decrease in time at least for 12 month, exhibits no observable food effect which deliver the opportunity of precise dosing and ease of administration of the reconstituted complex Lumacaftor in solution form.

Beneficial features of the present invention are as follows: the good/instantaneous redispersibility of solid complex formulations of Lumacaftor in water, biologically relevant media, e.g. physiological saline solution, pH=2.5 HCl solution, FaSSIF and FeSSIF media and gastro intestinal fluids and adequate stability in colloid solutions and/or dispersion in the therapeutic time window.

In an embodiment, the complex Lumacaftor formulation of the present invention has increased apparent solubility and permeability. In some embodiments, the apparent solubility and permeability of the complex Lumacaftor formulation is at least 1 mg/mL and $2 \times 10^{-6}$ cm/s in FaSSIF and FeSSIF biorelevant media, respectively.

In an embodiment, said complex possesses instantaneous redispersibility, has an apparent solubility in water of at least 1 mg/mL, and has a PAMPA permeability of at least $2 \times 10^{-6}$ cm/s in FaSSIF and FeSSIF biorelevant media.

In another embodiment, the complex Lumacaftor formulations of the present invention have an enhanced pharmacokinetic performance with improved solubility and permeability in fasted and fed state simulation that is expected to deliver full absorption and the elimination of the food effect.

BRIEF DESCRIPTION OF THE DRAWINGS

The accompanying figures, which are incorporated and form part of the specification, merely illustrate certain embodiments of the present invention and should not be construed as limiting the invention. They are meant to serve to explain specific modes of the present invention to those skilled in the art.

FIG. 1. shows redispersibility of complex Lumacaftor compositions in ultrapurified water.

FIG. 2. shows redispersibility and PAMPA permeability of complex Lumacaftor compositions in purified water.

FIG. 4. shows optimization of production parameters.

FIG. 11. shows apparent solubility of Lumacaftor formulations.

FIG. 12. shows PAMPA permeability of Lumacaftor formulations.

EXAMPLES

Specific embodiments of the present invention will further be demonstrated by the following examples. It should be understood that these examples are disclosed only by way of illustration and should not be construed as limiting the scope of the present invention.

Selection of Complex Lumacaftor Formulations with Improved Material Properties

Several complexation agents and pharmaceutically acceptable excipients and their combinations were tested in order to select the formulae having instantaneous redispersibility as shown in FIG. 1.

Examples that displayed an acceptable level of redispersibility were selected for further analysis.

PAMPA permeability of the selected formulations was measured in order to select complex Lumacaftor formulation having the best in-vitro performance (FIG. 2). PAMPA permeability measurements were performed as described by M. Kansi et al. (Journal of medicinal chemistry, 41, (1998) pp 1007) with modifications based on S. Bendels et al (Pharmaceutical research, 23 (2006) pp 2525). Permeability was measured in a 96-well plate assay across an artificial membrane composed of dodecane with 20% soy lecithin supported by a PVDF membrane (Millipore, USA). The receiver compartment was phosphate buffered saline (pH 7.0) supplemented with 1% sodium dodecyl sulfate. The assay was performed at room temperature; incubation time was 4 hours in ultrapurified water, FaSSIF and FeSSIF, respectively. The concentration in the receiver compartment was determined by UV-VIS spectrophotometry (VWR UV-3100PC Scanning Spectrophotometer).

Copolymer of vinylpyrrolidone and vinylacetate was selected as complexing agents and sodium lauryl sulfate was selected as pharmaceutically acceptable excipient in order to prepare complex Lumacaftor formulations having improved material characteristics.

Figure 3:
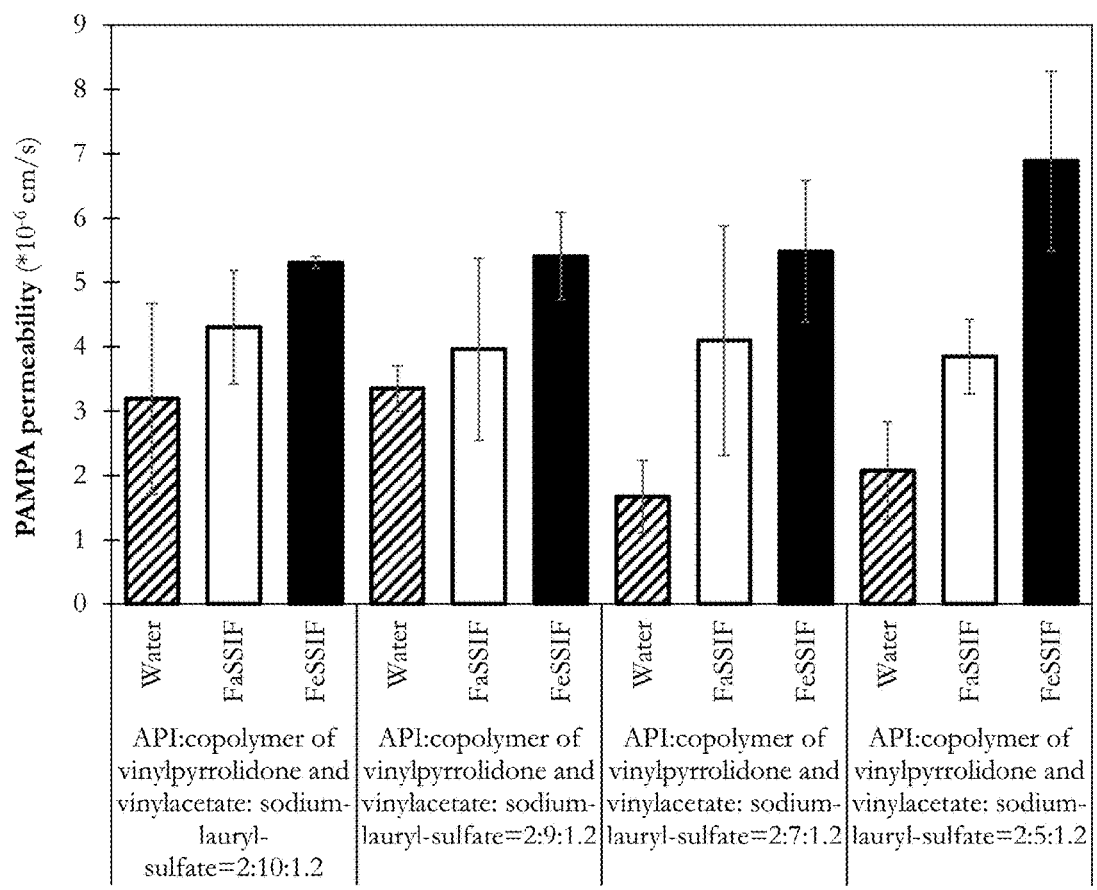
FIG. 3. shows PAMPA permeability of complex Lumacaftor formulations containing vinylpyrrolidone and vinylacetate copolymer and sodium lauryl sulfate in different ratios.

Solid complexes of Lumacaftor were prepared by using different ratios of complexation agent and pharmaceutically acceptable excipient. PAMPA permeability measurements were used to select the best performing complex formulation (FIG. 3). The best performing ratio of the copolymer of vinylpyrrolidone and vinylacetate: sodium lauryl sulfate: Lumacaftor (API) was found to be 9:1.2:2.

Production of Complex Lumacaftor Formulations

A solution mixture of Lumacaftor complex formulation was prepared by continuous flow mixing approach. 20 mL Solution 1 was prepared by dissolving 40 mg Lumacaftor and 180 mg copolymer of vinylpyrrolidone and vinylacetate in 20 mL methanol. The prepared Solution 1 was mixed with Solution 2 containing 24 mg sodium lauryl sulfate in 80 mL water at 1:4 volume ratio in order to produce complex Lumacaftor formulation with different flow rates. The solution mixture of the complex Lumacaftor formulation was produced at atmospheric pressure and ambient temperature. The appearance and the particle size of the produced colloid solution were monitored. Based on the physical appearance and particle size of the produced complex Lumacaftor formulation in colloid solution, the best composition was selected for further experiments (FIG. 4). The produced solution mixture was frozen on dry-ice and then it was lyophilized using a freeze drier equipped with −110° C. ice condenser, with a vacuum pump. Spray-drying was also applicable to produce solid powder from the solution mixture of complex Lumacaftor formulation.

In order to make the production process industrially feasible process intensification was performed by increasing the concentrations of the starting solutions. A colloid solution of complex Lumacaftor formulation of the present invention was prepared by mixing process. Solution 1 containing 200 mg Ivacaftor and 900 mg copolymer of vinylpyrrolidone and vinylacetate in 20 mL methanol was mixed with aqueous Solution 2 containing 120 mg sodium lauryl sulfate in 80 mL ultrapurified water at 1:4 volume ratio in order to produce complex Lumacaftor formulation. The produced solution mixture was frozen on dry-ice and then it was lyophilized using a freeze drier equipped with −110° C. ice condenser, with a vacuum pump. Spray-drying was also applicable to produce solid powder from the solution mixture of complex Lumacaftor formulation.

Preparation of Liquid Dispersible Granules Comprising Complex Lumacaftor Formulation Liquid dispersible granules comprising the complex Lumacaftor formulations of the present invention can be obtained by wet or dry granulation processes.

Dry granulation process includes, but not limited to the slugging or roll compaction of the powder formulation of complex Lumacaftor into compacts and breaking of the compacts into granules with appropriate mesh size. The obtained granules can be mixed with excipients chosen from the group consisting of fillers, extenders, binders, disintegrating agents, wetting agents, lubricants, taste masking, sweetening, flavoring, and perfuming agents.

Dry granulation technique can be also applied on the powder blend of complex Lumacaftor formulations. Powder blend consists of the powder formulation of complex Lumacaftor and excipients chosen from the group consisting of fillers, extenders, binders, disintegrating agents, wetting agents, lubricants, taste masking, sweetening, flavoring, and perfuming agents and prepared by mixing of powders. Slugging or roll compaction are used to manufacture compacts from the powder blend. Then the compacts are broken into granules with appropriate mesh size.

Wet granulation process covers the moisturizing of the powder formulations of complex Lumacaftor (direct granulation) or moisturizing the excipients chosen from the group consisting of fillers, extenders, binders, disintegrating agents, wetting agents, lubricants, taste masking, sweetening, flavoring, and perfuming agents with aqueous solution of pharmaceutically acceptable binders and mixing it with the powder formulations of complex Lumacaftor (indirect granulation). The particle size of the granules can be controlled by physical impact before and after the drying step.

Liquid dispersible granules of complex Lumacaftor formulation of the present invention were prepared by compacting appropriate amount of complex Lumacaftor powder blend using 0.5 ton load. The powder blend comprised of the solid formulation of the complex of Lumacaftor and, optionally, sweetening, flavoring, aromatizing and perfuming agents. The height of the compact was found to be optimal between 0.8-1.0 mm. The compacts were broken up by physical impact to form granulates. The particle size of the granules was controlled by sieving with appropriate mesh size to achieve 160-800 micrometers particle size. The Hausner-ratio of the granule was between 1.00 and 1.18 and the Carr's index was ≤15.

Comparative Solubility Tests

The apparent solubility of complex Lumacaftor formulation of the present invention was measured by UV-VIS spectroscopy at room temperature. The solid complex Lumacaftor formulations were dispersed in ultrapurified in 1, 10 and 20 mg/mL Lumacaftor equivalent concentration range. The resulting solutions were filtered by 100 nm disposable syringe filter. The Lumacaftor content in the filtrate was measured by UV-Vis spectrophotometry and the apparent solubility was calculated. The filtrate may contain Lumacaftor complex particles which could not be filtrated out using 100 nm pore size filter.

The apparent solubility of complex Lumacaftor formulation of the present invention was 0.950, 9.839 and 14.913 mg/mL, when 1, 10 and 20 mg/mL Lumacaftor equivalent formulations were dispersed in ultrapurified water, respectively. The apparent solubility of unformulated crystalline Lumacaftor was found to be 0.032 mg/mL.

Solubility of complex Lumacaftor formula was 1 mg/mL.

Comparative Dissolution Tests

Comparative dissolution tests were performed by dispersing 1 mg/mL Lumacaftor equivalent complex Lumacaftor formulation and crystalline Lumacaftor in 15 mL FaSSIF and FeSSIF media under stirring. The dissolved amount was measured with HPLC after filtration with 220 nm pore size filter at different time points. Dissolution of Lumacaftor from the complex formulation was instantaneous, while the dissolution of crystalline Lumacaftor was slower (FIG. 4). Within 10 minutes the Lumacaftor dissolution from the complex formulation of the present invention was almost complete (100%), while it was below 1% from the crystalline Lumacaftor.

Comparative In-Vitro PAMPA Assays

Since Lumacaftor should be administered with food in order to improve its biological performance, PAMPA permeabilities of amorphous Lumacaftor, crystalline Lumacaftor and complex Lumacaftor formulation were measured and compared in simulated fasted state. PAMPA permeability of amorphous Lumacaftor, crystalline Lumacaftor and complex Lumacaftor formulation was $1.1798 \times 10^{-6}$ cm/s, $0.53053 \times 10^{-6}$ cm/s and $3.9615 \times 10^{-6}$ cm/s, respectively.

Stability of the Complex Lumacaftor Formulation in Solid Form

Figure 5:
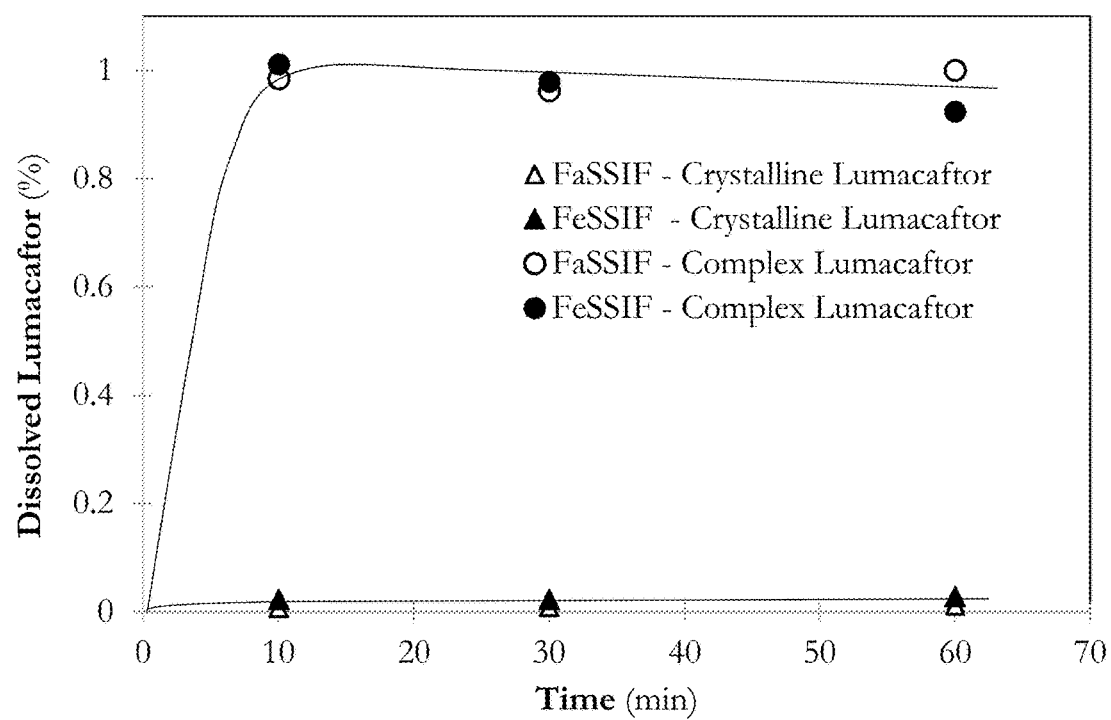
FIG. 5. shows Lumacaftor dissolution from crystalline Lumacaftor and complex Lumacaftor formulation.

PAMPA permeabilities of the solid complex Lumacaftor formulations were used to monitor the physical stability of the formulations. PAMPA permeability was measured in FaSSIF biorelevant media and after storage at different conditions. 1 month storage at RT or 40° C. 75% relative humidity showed no significant decrease in the measured PAMPA permeability (FIG. 5).

Structural Analysis

Figure 6:
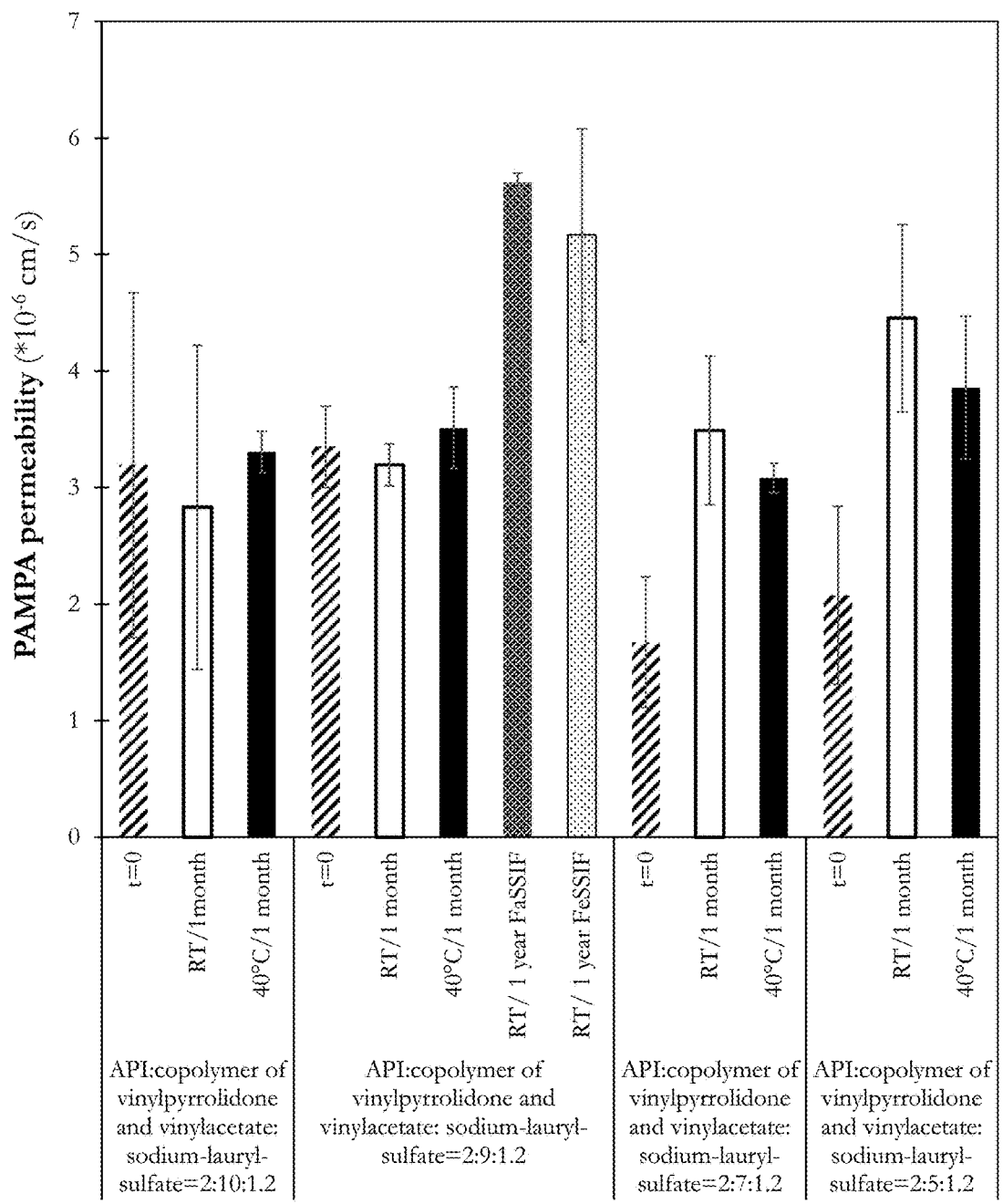
FIG. 6. shows PAMPA permeabilities of Lumacaftor formulations measured at different time points.

Morphology of complex Lumacaftor formulation was investigated using FEI Quanta 3D scanning electron microscope. Complex Lumacaftor formulation of the present invention comprises spherical particles in the size range of less than 100 nm (FIG. 6).

Structural analysis was performed by using Vertex 70 FT-IR with ATR and HORIBA JobinYvon LabRAM HR UV-VIS-NIR instruments.

Figure 7:
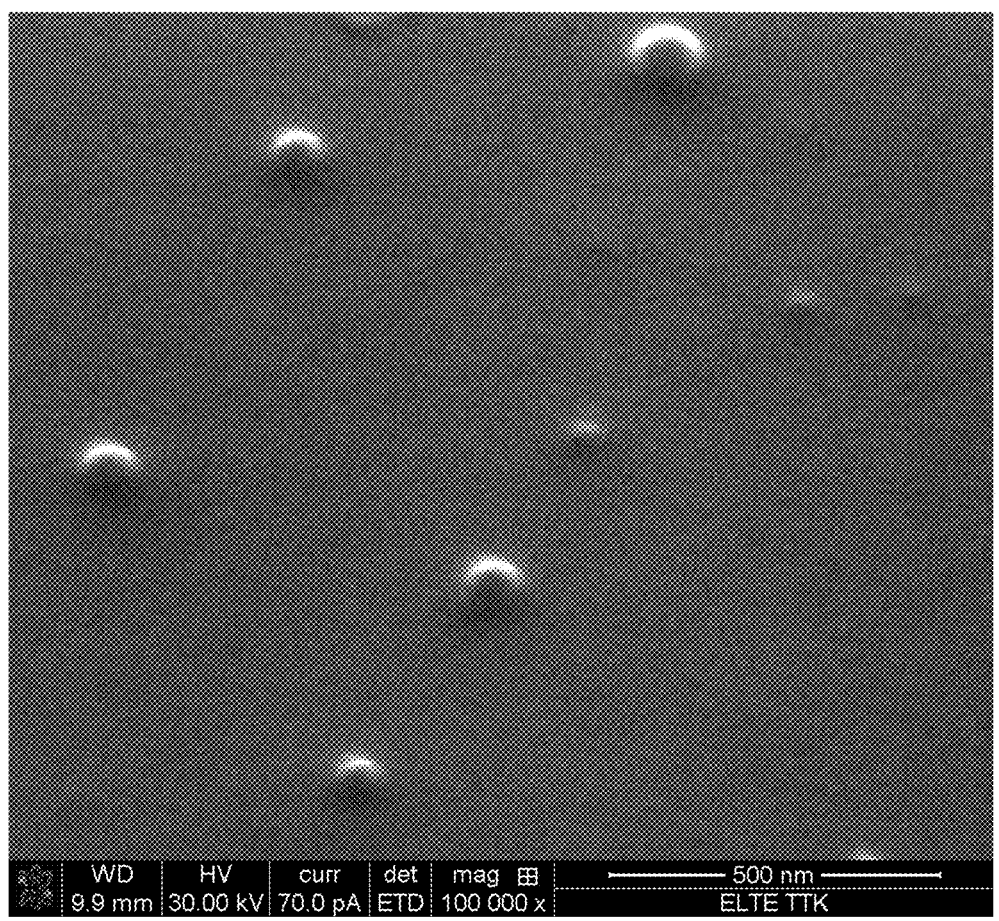
FIG. 7. shows SEM photo of complex Lumacaftor formulation.

Complex Lumacaftor formulation or its pharmaceutical composition is characterized by characteristic Raman shifts at 553 $cm^{-1}$, 602 $cm^{-1}$, 635 $cm^{-1}$, 654 $cm^{-1}$, 747 $cm^{-1}$, 841 cm⁻¹, 899 cm⁻¹, 934 cm⁻¹, 1002 cm⁻¹, 1021 cm⁻¹, 1117 cm⁻¹, 1205 cm⁻¹, 1232 cm⁻¹, 1310 cm⁻¹, 1352 cm⁻¹, 1372 cm⁻¹, 1428 cm⁻¹, 1444 cm⁻¹, 1497 cm⁻¹, 1592 cm⁻¹, 1609 cm⁻¹, 1677 cm⁻¹ and 1737 cm⁻¹ shown in FIG. 7.

Complex Lumacaftor formulation or its pharmaceutical composition is characterized by characteristic Raman shifts at 553 cm⁻¹, 654 cm⁻¹, 747 cm⁻¹, 841 cm⁻¹, 899 cm⁻¹, 1117 cm⁻¹, 1205 cm⁻¹, 1310 cm⁻¹, 1372 cm⁻¹, 1428 cm⁻¹, 1677 cm⁻¹ and 1737 cm⁻¹.

Figure 8:
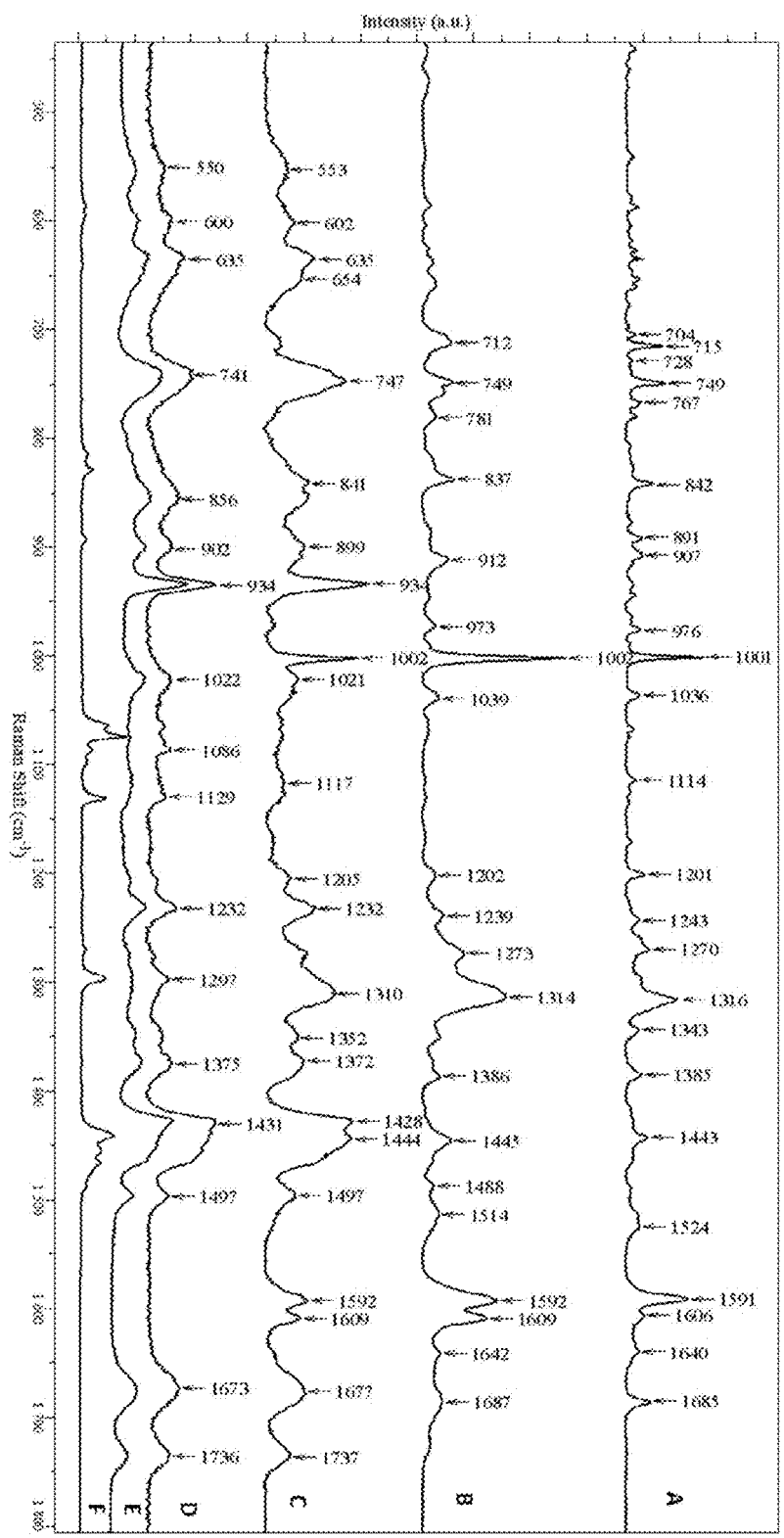
FIG. 8. shows Raman spectra of crystalline Lumacaftor (A), amorphous Lumacaftor (B), complex Lumacaftor formulation (C), placebo (D), Luviscol VA64 (E), SDS (F).

Complex Lumacaftor formulation or its pharmaceutical composition is characterized by characteristic infrared (ATR) peaks at 635 cm⁻¹, 703 cm⁻¹, 747 cm⁻¹, 837 cm⁻¹, 1021 cm⁻¹, 1165 cm⁻¹, 1231 cm⁻¹, 1288 cm⁻¹, 1369 cm⁻¹, 1423 cm⁻¹, 1462 cm⁻¹, 1494 cm⁻¹, 1667 cm⁻¹ and 1731 cm⁻¹ shown in FIG. 8.

Complex Lumacaftor formulation or its pharmaceutical composition is characterized by characteristic infrared (ATR) peaks at 703 cm⁻¹, 837 cm⁻¹, 1231 cm⁻¹, 1369 cm⁻¹ and 1667 cm⁻¹.

Figure 9:
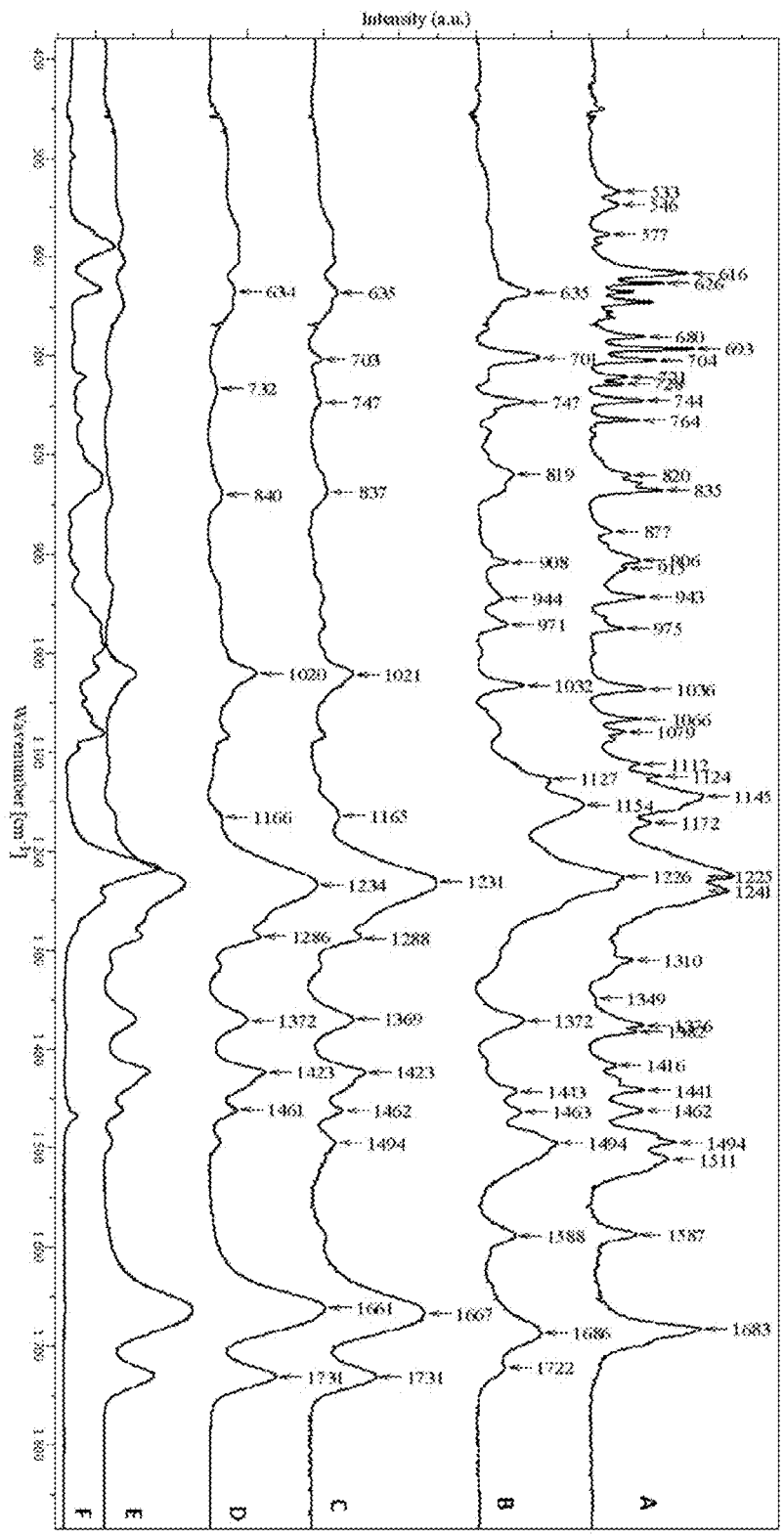
FIG. 9. shows ATR spectra of crystalline Lumacaftor (A), amorphous Lumacaftor (B), complex Lumacaftor formulation (C), placebo (D), Luviscol VA64 (E), SDS (F).

The structure of the complex Lumacaftor formulation of the present invention was investigated by powder X-ray diffraction (XRD) analysis (Philips PW1050/1870 RTG powder-diffractometer). The measurements showed that the Lumacaftor in the complex formulations was XRD amorphous (FIG. 9). Characteristic reflections on the diffractograms of complex Lumacaftor formulation at 43 and 44 2Theta could be attributed to sample holder.

Based on in-vitro data which shows fast and full dissolution and increased permeability in fasted and fed state simulation it is expected that the complex Lumacaftor formulation delivers full absorption and the elimination of the food effect.

Comparative Formulation Studies

Crystalline Lumacaftor was ball milled in the absence of complexation agent (Luviscol VA64) and pharmaceutically acceptable excipient (SDS) and in the presence of them. Ball milling parameters were the following:

Speed: 500 rpm
Milling time: 1 hour
Number of the balls: 25 pcs with 10 mm diameter
Milling vessel's material: Si₂N₃
Quantity of the milled samples: 100 mg API equivalent mass in 12 mL Milli-Q water After the milling the vessel was washed out with 5 mL Milli-Q water. The product was frozen on salted ice and then it was lyophilized using a freeze drier equipped with −110° C. ice condenser, with a vacuum pump. The material and in-vitro properties of the resulted formulations were compared to the complex Lumacaftor formulation of the present invention.

Particle size of the formulations was measured in reconstituted dispersion/solution. It was d(90)=782 nm and d(90)=282 nm for the ball milled Lumacaftor with Kollidon VA64 and SDS and complex Lumacaftor formulation, respectively. Ball milled crystalline Lumacaftor was hardly redispersible in purified water resulting in a suspension with visible particles, the particle size could not be determined.

Figure 10:
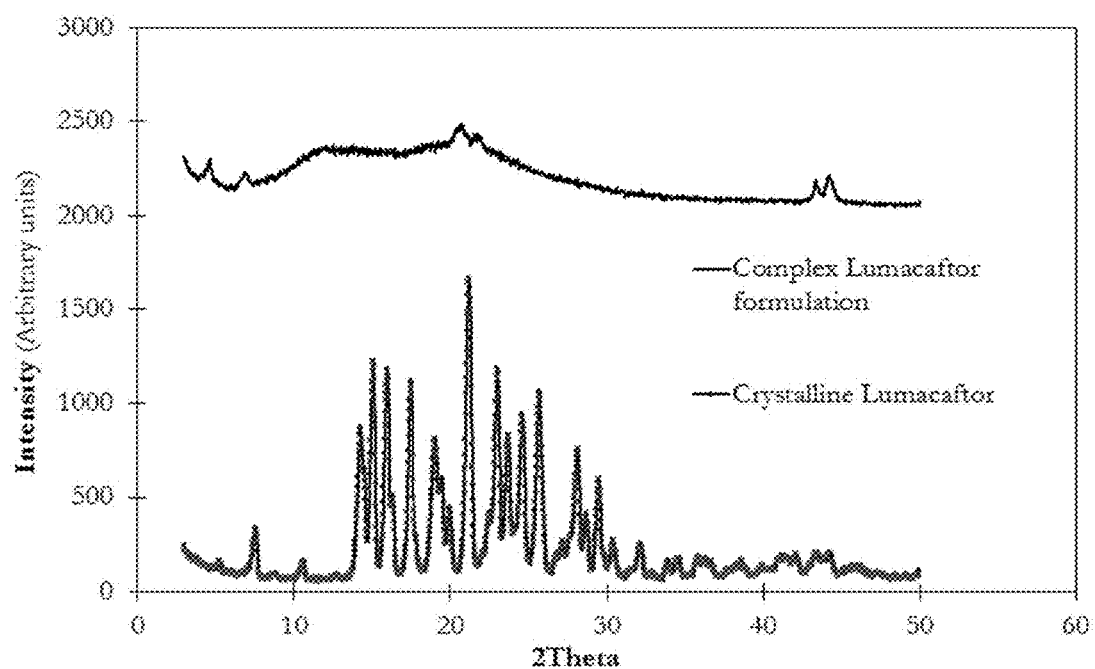
FIG. 10. shows XRD diffractograms of crystalline Lumacaftor and complex Lumacaftor formulation.

Apparent solubility of complex Lumacaftor formulation was 14.913 mg/mL when 20 mg Lumacaftor equivalent formulation was redispersed (FIG. 10).

PAMPA permeability of the formulations was measured in FaSSIF biorelevant media and compared. PAMPA permeability of the complex Lumacaftor formulation was 4.651×10⁻⁶ cm/s, while it was 0.288×10⁻⁶ cm/s for the ball milled crystalline Lumacaftor (FIG. 11).

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A stable complex comprising
   i. Lumacaftor;
   ii. At least 50% by weight of a complexation agent which is a copolymer of vinylpyrrolidone and vinyl acetate; and
   iii. Sodium lauryl sulfate;
   wherein the ratio of the copolymer:sodium lauryl sulfate:Lumacaftor is 9:1.2:2, and
   wherein said complex has a particle size is between 10 nm and 500 nm, and possesses one or more among the following features:
   a) has an apparent solubility in water of at least 1 mg/mL; and
   b) has a PAMPA permeability of at least 2×10⁻¹ 2 3 4 cm/s when dispersed in FaSSIF or FeSSIF biorelevant media, which does not decrease in time at least for 12 month.

2. The complex as recited in claim 1, wherein said complex has a particle size in the range between 10 nm and 250 nm.

3. The complex as recited in claim 1, wherein said complex exhibits X-ray amorphous character in the solid form.

4. The complex as recited in claim 1, wherein said complex has an apparent solubility in water of at least 1 mg/mL and a PAMPA permeability of at least 2×10⁻⁶ cm/s in FaSSIF and FeSSIF biorelevant media.

5. The complex as recited in claim 1 comprising
   a) Lumacaftor;
   b) a complexation agent which is a copolymer of vinylpyrrolidone and vinylacetate; and
   c) a pharmaceutically acceptable excipient which is sodium lauryl sulfate;
   wherein said complex is characterized by infrared (ATR) peaks at 635 cm⁻¹, 703 cm⁻¹, 747 cm⁻¹, 837 cm⁻¹, 1021 cm⁻¹, 1165 cm⁻¹, 1231 cm⁻¹, 1288 cm⁻¹, 1369 cm⁻¹, 1423 cm⁻¹, 1462 cm⁻¹, 1494 cm⁻¹, 1667 cm⁻¹ and 1731 cm⁻¹; and
   is characterized by Raman shifts at 553 cm⁻¹, 602 cm⁻¹, 635 cm⁻¹, 654 cm⁻¹, 747 cm⁻¹, 841 cm¹, 899 cm⁻¹, 934 cm⁻¹, 1002 cm⁻¹, 1021 cm⁻¹, 1117 cm⁻¹, 1205 cm⁻¹, 1232 cm⁻¹, 1310 cm⁻¹, 1352 cm⁻¹, 1372 cm⁻¹, 1428 cm⁻¹, 1444 cm⁻¹, 1497 cm⁻¹, 1592 cm⁻¹, 1609 cm⁻¹, 1677 cm⁻¹ and 1737 cm⁻¹.

6. A pharmaceutical composition comprising the stable complex as recited in claim 1 together with one or more pharmaceutically acceptable carriers.

7. The pharmaceutical composition as recited in claim 6, wherein said composition is suitable for oral, pulmonary, rectal, colonic, parenteral, intracisternal, intravaginal, intraperitoneal, ocular, otic, local, buccal, nasal, or topical administration.

8. The pharmaceutical composition as recited in claim 7, wherein said composition is suitable for oral administration.

9. The pharmaceutical composition comprising the complex according to claim 8, wherein said composition comprises fast dissolving granules of the complex formulation according to claim 1.

10. The pharmaceutical composition comprising the complex according to claim 9, wherein said granules are suitable for the preparation of sachet dosage form.

11. The complex as recited in claim 1, wherein
said complex is not obtained via a milling process, high pressure homogenization process, encapsulation process or solid dispersion processes.

12. The complex as recited in claim 1, wherein said complex further comprises one or more additional active agents.

13. The complex as recited in claim 12, wherein said additional active agent Ivacaftor, Tezacaftor or chosen from agents used for the treatment of CFTR mediated diseases.

14. The complex as recited in claim 1, wherein said complex is instantaneously redispersable in physiological relevant media.

15. The complex as recited in claim 1, wherein said complex is stable in solid form and in colloid solution and/or dispersion.

* * * * *